(12) United States Patent
Cheng et al.

(10) Patent No.: US 6,800,768 B1
(45) Date of Patent: Oct. 5, 2004

(54) NON-NUCLEOSIDIC COUMARIN DERIVATIVES AS POLYNUCLEOTIDE-CROSSLINKING AGENTS

(75) Inventors: Peter C. Cheng, San Jose, CA (US); Tadashi J. Mizoguchi, Santa Clara, CA (US)

(73) Assignee: Naxcor, Inc., Mountain View, CA (US)

( * ) Notice: Subject to any disclaimer, the term of this patent is extended or adjusted under 35 U.S.C. 154(b) by 0 days.

(21) Appl. No.: 10/655,021

(22) Filed: Sep. 5, 2003

Related U.S. Application Data

(60) Provisional application No. 60/408,633, filed on Sep. 6, 2002.

(51) Int. Cl.[7] .................. C07D 311/14; C07D 311/16
(52) U.S. Cl. ........................... 549/289; 549/290
(58) Field of Search .................... 549/289, 290

(56) References Cited

U.S. PATENT DOCUMENTS 6,005,093 A * 12/1999 Wood et al. ............... 536/24.3

OTHER PUBLICATIONS

El–Ansary et al, Egypt J. Pharm. Sci., vol. 33, No. 3–4, pp. 639–650, 1992.*

* cited by examiner

*Primary Examiner*—Ba K. Trinh
(74) *Attorney, Agent, or Firm*—Ralph T. Lilore

(57) ABSTRACT

Novel coumarin derivatives comprising a coumarin moiety linked to a non-nucleosidic backbone moiety are disclosed. The resulting molecules are typically used as photoactivate crosslinking groups when incorporated into polynucleotides as replacements for one or more of the complementary nucleoside bases present in probes used in procedures involving nucleic acid hybridization reactions.

32 Claims, No Drawings

NON-NUCLEOSIDIC COUMARIN DERIVATIVES AS POLYNUCLEOTIDE-CROSSLINKING AGENTS

This application claims benefit of 60/408,633 filed Sep. 6, 2002.

TECHNICAL FIELD

This invention is related to photoactive nucleoside analogs that can be incorporated into synthetic oligonucleotides during automated DNA synthesis for use in crosslinking of complementary target nucleic acid sequences.

BACKGROUND

The use of crosslinkable probes in nucleic acid hybridization assays to crosslink to target sequences is demonstrated in U.S. Pat. No. 4,826,967 byGlass.; compounds are based on furocoumarin (or psoralen) attached to existing polynucleotides (usually through adduct formation) and are satisfactory for many applications. However, the crosslinking group/nucleoside adduct is difficult to synthesize, particularly in large quantities. In U.S. Pat. No. 5,082,934, Saba et al. describe a photoactivatible nucleoside analog comprising a coumarin moiety linked through its phenyl ring to the 1-position of a ribose or deoxyribose sugar moiety in the absence of an intervening base moiety. The resulting nucleoside analog is used as a photo-crosslinking group when inserted into a polynucleotide as a replacement for one or more of the complementary nucleoside bases present in a probe used in hybridization assays.

Nevertheless, new types of compounds that offer additional advantages, such as stability throughout probe synthesis and use, and conformational flexibility, continue to remain desirable.

SUMMARY OF THE INVENTION

The current invention provides non-nucleosidic, stable, photoactive compounds that can be used as photo-crosslinking reagents in nucleic acid hybridization assays and therapeutic applications, as well as techniques and intermediates that can be used to prepare the final products.

The compounds comprise coumarinyl derivatives prepared by linking the phenyl ring of a coumarin molecule or derivative to a hydroxy or polyhydroxy hydrocarbon molecule, such as one of the terminal hydroxy groups of a glycerol molecule. Not to be limited by theory, it is considered that the (poly)hydroxy hydrocarbon moiety of the resulting compound is equivalent to the sugar of a nucleoside, whereas the coumarin moiety occupies the position of a base. Accordingly, the compounds can be inserted into growing polynucleotide chains using automated (or manual) techniques of polynucleotide synthesis. The double bond between the 3- and 4-positions of the coumarin ring system is a photoactive group that covalently crosslinks to nucleosides in the complementary strand when an oligonucleotide containing this non-nucleoside analog (the "probe") is used in a hybridization assay and/or therapeutic application.

For the most part, the photoactive compound has the formula:

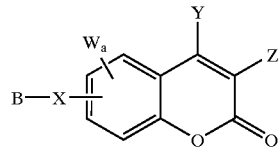

in which the substituents and linking groups are described below in more detail.

The (poly)hydroxy hydrocarbon backbones give maximum flexibility and stability to the oligosaccharide structure in which they are located as well as good solubility in aqueous and organic media.

DESCRIPTION OF SPECIFIC EMBODIMENTS

Whereas multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

The present invention provides crosslinkable compounds that can be used as a photoactivatible non-nucleosidic crosslinker in oligonucleotide probes used in hybridization assays and/or therapeutic applications. In hybridization assays, the compounds of the inventions are typically used as part of synthetic DNA or RNA oligonucleotides to determine the presence or absence of a specific DNA and RNA base sequence in a sample. More specifically, this invention provides coumarin derivatives attached to a stable, flexible, (poly)hydroxy hydrocarbon backbone unit that act as photoactive crosslinking compounds in hybridization assays.

Compounds of the invention have the general formula:

Backbone Moiety—Linking Moiety—Crosslinking Moiety

"Moiety" here and elsewhere in this specification indicates a part of a molecule that performs the indicated function. A given moiety is usually derived from another molecule by covalently linking together two or more molecules, with the identifiable remnants of the original molecules being referred to as "moieties." For example, if a psoralen molecule is attached to a glycerin molecule with a divalent linker, such as a methylene group, the resulting single molecule is referred to as being formed of glycerin, methylene, and psoralen moieties. It is not necessary, however, that the three moieties actually arose from three separate molecules, as discussed below. Thus "derived from" can refer to theoretical, as well as actual, precursors.

The crosslinking moiety will be derived from molecules having a fused benzopyrone structure, such as the following: (1) coumarin and its simple derivatives; (2) psoralen and its derivatives, such as 8-methoxypsoralen or 5-methoxypsoralen (at least 40 other naturally occurring psoralens have been described in the literature and are useful in practicing the present invention); (3) cis-benzodipyrone and its derivatives; (4) trans-benzodipyrone; and (5) compounds containing fused coumarin-cinnoline ring systems.

All of these molecules contain the necessary crosslinking group (an activated double bond) with the potential to crosslink with a nucleotide in the target strand. All of these molecules are coumarin derivatives, in that each contains the basic coumarin (benzopyrone) ring system on which the remainder of the molecule is based.

The linking moiety will normally be formed from a precursor that contains from about 1 to about 100, for example; from about 1 to 25, or from about 1 to about 10, atoms with functional groups at two locations for attaching the other moieties to each other. After reaction of the precursor to form the linking moiety, the total number of atoms in the shortest linking chain of atoms between the coumarin ring system and the backbone moiety (sugar substitute) is generally from about 1 to about 15, for example, from about 1 to about 7, or from about 1 to about 3. Otherwise this part of the structure can vary widely, as this is essentially just a flexible linkage from the crosslinking moiety to the backbone moiety.

The linking moiety is most often a stable cyclic or acyclic moiety derived by reaction of a molecule bearing appropriate functional groups (usually at its termini) for linking the crosslinking molecule at one end and the backbone molecule at the other end. However, if sufficient functional groups are present in the backbone and crosslinking moieties, a precursor to the linking moiety need not be used (i.e., the backbone and crosslinking moieties can be connected by a covalent bond).

It should be recognized that the description of a particular part of the final molecule as belonging to a particular moiety of those identified above is somewhat arbitrary and does not necessarily mean that there were three original molecules that reacted to form the final product. There are a number of coumarin derivatives, for example, that have a fuctionalized methyl or methoxy group attached to the coumarin ring that can react with a functional group on a backbone moiety precursor to form a product from only two starting materials. However, the resulting structure will generally appear to have three parts as indicated above: the backbone molecule that is incorporated into the sugar backbone of a polynucleotide, the crosslinking moiety that occupies the space occupied by a base in a normal nucleoside, and the atom or atoms (i.e., the linking moiety) that join the two principal parts together. For the sake of convenience, the linking moiety is considered to consist of atoms between the ring atom of the crosslinking moiety at the point of attachment and the nearest contiguous atom that clearly forms part of the backbone structure in the moiety that replaces the sugar molecule, which is usually the carbon atom bearing a hydroxy group (or reaction product of a hydroxy group).

The backbone moiety, so called because it ultimately functions in place of the ribose or deoxyribose portion of the backbone of a polynucleotide, will generally have 1 to 3 (sometimes more) hydroxy groups (or similar functional groups, as discussed below) attached to different $sp^3$- hybridized carbon atoms. The backbone moiety is generally uncharged so that it can function as a substitute for ribose or deoxyribose in the final modified nucleotide. Backbone moieties include but are not limited to the following: (1) linear hydrocarbon moieties such as a three-carbon propane unit or a longer hydrocarbon chain with appropriate functional groups, usually selected from the group consisting of —OH, —$NH_2$, —SH, —COOH, acid halides, and acid anhydrides, and (2) cyclic hydrocarbon moieties typically having a 5- to 7-membered carbon ring structure bearing one to three hydroxy groups or other functional groups as in (1) above. The functional groups declared in the preceding sentence may refer to unreacted forms and may be present as derivatives of the indicated functional groups in many embodiments. The reactive functional groups mentioned above (other than —OH and —SH) are generally present only in intermediates; however, after reacting with other functional groups, they become stable groups or form covalent bonds to other parts of the molecule.

In addition to the basic structure described above, one or more coupling moieties can be attached to the backbone moiety to facilitate formation of bonds to existing or growing polynucleotide chains. The coupling moieties will typically comprise hydroxy coupling and/or protecting groups that are used in solution or solid-phase nucleic acid synthesis when the molecule in question is an intermediate being used in the preparation of a probe molecule. Typical coupling moieties include phosphoramidite, phosphate, H-phosphonate, phosphorothioate, methyl phosphonate, trityl, dimethoxytrityl, monomethoxytrityl, and pixyl derivatives. Non-phosphorus coupling moieties include carbamate, amide, and linear and cyclic hydrocarbon derivatives, typically connecting to the remainder of the molecule with heteroatom substituents, such as —$COCH_3$, —$CH_2OH$, —$CF_3$, —$NHCH_3$, and —$PO_2CH_2CH_3$. For a review of such chemistry, see "Oligonucleotide Synthesis: A Practical Approach," Gait, M. J., Ed., IRL Press, 1984, which is herein incorporated by reference.

In certain aspects, compounds of the invention have the formula:

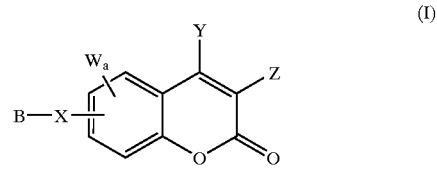

(I)

wherein
  B represents (1) a linear, branched, or cyclic hydrocarbon group containing from about 2 to 15, for example, from about 3 to about 10, or from about 3 to about 6, carbon atoms and, if cyclic, containing a 5- or 6-membered ring or (2) a heterocyclic aromatic ring system comprising a 5- or 6-membered ring, both of B(1) and B(2) being substituted with 1, 2, or 3 groups of the formula $OR_1$;
  X represents (1) a linear, branched, or cyclic hydrocarbon group containing from about 1 to about 15, for example, from about 2 to about 10, or from about 3 to about 6, carbon atoms or (2) such an X(1) group in which one to three carbon atoms of the hydrocarbon group are replaced by an oxygen, sulfur, or nitrogen atom and in which the shortest linking chain of atoms in X between atoms in other parts of the formula attached to X is 1 to 10 atoms, wherein X is optionally substituted with 1 to 3 substituents selected from the group consisting of hydroxy, halo, amino, amido, azido, carboxy, carbonyl, nitro, thio, perfluoromethyl, and cyano functional groups;
  each W independently represents a hydroxy, halo, amino, amido, azido, nitro, thio, carboxy, carbonyl, perfluoromethyl, or cyano functional group; an unsubstituted hydrocarbyl group of about 10 or fewer carbon atoms, for example, about 6 or fewer, or about 3 or fewer; or such a hydrocarbyl group substituted with 1 to 3 of the functional groups or in which one carbon atom is replaced by an oxygen, sulfur, or nitrogen atom;

with the provisos that (1) when X or W is a substituted hydrocarbon, the total number of substituents in X or W is less than the total number of carbon atoms in the X or W and no more than one substituent or heteroatom is attached to a given carbon, unless the substituents are halogen atoms on the given carbon; (2) the total carbon atoms in all W substituents is about 15 or fewer, for example, about 10 or fewer, or about 6 or fewer; and (3) two W's together can form a ring when taken together with the remainder of the atoms to which they are attached (e.g., as in a psoralen);

Y and Z independently represent H, F, or lower alkyl (usually about 5 or fewer carbons, for example, about 3 or fewer); and each $R_1$ independently represents H or a hydroxyl-protecting or hydroxyl-coupling group capable of protecting or coupling a hydroxy group during synthesis of a polynucleotide, or one or two (in certain embodiments, two) $R_1$ groups represent a nucleotide or a polynucleotide connected to the compound.

The oxygen atom or other non-carbon atom (if present) of a functional group (such as an ether or carboxylate) that bridges the B—X linkage often arises from a hydroxy group in the precursor of B, but is considered part of the X linker (for ease of defining the various groups) in this and the following formulas, unless the contrary is clear from the context of the discussion.

Within general formula 1 depicted above, certain compounds are generally acceptable. The most important part of the molecule (at least in view of the difference between these compounds and what was previously known) is the B or backbone moiety. In one aspect, B moieties belong to a group of a first sub-formula:

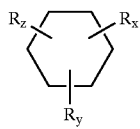

a group of a second sub-formula:

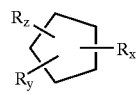

or a group of a third sub-formula:

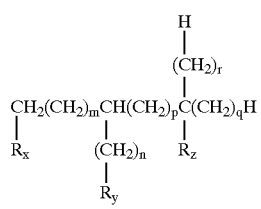

wherein $R_x$, $R_y$, and $R_z$ independently represent H or $OR_1$;

m, n, p, q, and r independently represent 0 or 1;

one hydrogen of the sub-formula is replaced by a covalent bond to the X group; and all other substituents and definitions of the formula of the compound are as previously defined for general formula I.

The hydrogen atom of the sub-formula that is replaced by a covalent bond to the X group is usually a hydrogen of a hydroxy group (i.e., at least one $OR_1$ would represent a hydroxy group in such a precursor molecule). However, this choice is for convenience of synthesis only, as the resulting B—X linkage can readily be prepared from (poly)hydroxy hydrocarbon precursors, many of which are commercially available. Other hydrogens can be replaced by the indicated covalent bond if desired. The actual molecules used in synthesis are often still derived from a (poly)hydroxy compound in which one of the hydroxy groups has been replaced by the functional group, often through a series of reactions. For example, a hydroxy group can be replaced by a halogen atom or other leaving group, and the leaving group can participate in bond formation with an electron donating group in the precursor of the X group.

Compounds in which B is formed from a saturated hydrocarbon are utilized in certain embodiments, although unsaturated compounds (including cyclic aromatics) are permitted. In unsaturated compounds (including aromatics), the —$OR_1$ substituent is generally not attached directly to an $sp^2$-hybridized carbon, but is attached to an intervening $sp^3$ carbon, as in —$CZ_2OR_1$ in which each Z represents H or an alkyl group.

Compounds of formula I in which B has the third sub-formula are of particular interest among the three sub-formulas, especially those in which m+n+p+q+r=0, 1, or 2, In certain aspects, these compounds of the third sub-formula represent an acyclic, saturated, di- or tri-hydroxy hydrocarbon, especially glycerol and 1,2- or 1,3-dihydroxyalkanes of 3 to 5 carbons that are attached to the X group at the terminal position furthest from the indicated hydroxy groups, such as 4,5-dihydroxypentyl; 3,5-dihydroxypentyl; 2,4-dihydroxy-2-methylbutyl; 3-hydroxy-2-(hydroxymethyl)propyl; and 2,3-dihydroxypropyl.

Although such compounds are not selected, as already indicated, aromatic ring systems can be present in the B moiety. These include both hydrocarbon and heterocyclic aromatic ring systems. Of these compounds, those in which B comprises a benzene or naphthalene ring system are selected, especially 1,2-di(hydroxymethyl)-substituted aromatics. The same substituents are chosen when B comprises a heterocyclic ring system, such as a furan, pyran, pyrrole, pyrazole, imidazole, piperidine, pyridine, pyrazine, pyrimidine, pyrazidine, thiophene, acridine, indole, quinoline, isoquinoline, quinazoline, quinoxaline, xanthene or 1,2-benzopyran ring systems.

Also within the scope of the invention are compounds in which B comprises a bridged hydrocarbon ring system, such as a bicyclo[3.1.0]hexane or bicyclo[2.2.]heptane ring system. These molecules have configurations with reduced mobility so that various cis and trans substitution pattern can be easily prepared and maintained. See, for example, Ferguson, L. N. "Organic Molecular Structure," Willard Grant Press, 1975, Chapters 17–19, for a review of this chemistry and synthetic techniques. In a like manner, compounds in which B comprises a spiro or dispiro hydrocarbon ring system are also within the scope of the invention.

As previously noted, the X linking group is not particularly restricted in structure, as it is not present in a part of the molecule that interacts either with the remainder of the backbone structure or with a complementary strand of a polynucleotide. However, there are acceptable structures for this part of the molecule, such as the following, which can represent X, in either of the two possible orientations:

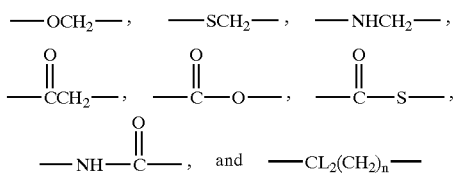

in which L represents H, F, Cl, I, or Br and n=0, 1, or 2.

Other acceptable compounds are those in which X comprises a cyclic structure with a 5- or 6-membered carbon or heterocyclic ring (the latter containing one O, S, or N atom), such as cyclopentane, cyclohexene, dihydrofuran, pyrrole, or pyridine.

In the crosslinking moiety, Y and Z generally contain about 5 or fewer carbon atoms, for example about 3 or fewer, and in certain embodiments are often methyl if they are alkyl groups. In certain aspects of the invention, W, Y, and Z are all hydrogen atoms, as are compounds in which W is a pyrone or furan ring fused to the phenyl ring of the formula. These latter compounds are among compounds in which all of the formula to the right of X in formula I represents coumarin, psoralen, cis-benzodipyrone, or trans-benzodipyrone or a derivative thereof within the formula.

The compounds of formula I in which a nucleotide or polynucleotide is connected to the compound are usually (but not always) connected via a phosphorus-containing linking group. Phosphorus-containing linking groups, as well as other linking groups, are discussed elsewhere. Such conjugates are desirable compounds of the invention, as they can be used directly in the assays and crosslinking processes that are the principal end use of this invention. These compounds have the formula $(N_{m1}Q_{m4}N_{m2})_{m3}$ in which each N independently represents a nucleotide of a desired polynucleotide sequence; Q represents the nucleotide-replacing molecule of the invention incorporated into the normal polynucleotide sequence; m1 and m2 are integers (usually less than 200, for example, less than about 100; one of m1 and m2 is usually at least 14, for example, at least about 17, or least about 20); m3 is an integer from about 1 to about 10, for example, from about 1 to about 5 (m3 is generally less than (m1+m2)/10); and m4 is from about 1 to about 5, for example, from about 1 to about 3. It is also possible to have two or more Q moieties separated from each other by a few (usually one or two) normal bases in a polynucleotide sequence as long as there is an uninterrupted sequence of nucleotides to make the hybrid stable. Such sequences are considered to be equivalent to uninterrupted Q sequences. Suitable lengths of uninterrupted normal nucleotide sequences are as declared above for m1 and m2.

Q can be present either in the interior of the polynucleotide or at a terminal position. In an interior position, at least two $R_1$ groups must be present in order to allow the Q molecule to connect to ends of two separate strands; if Q is inserted at a terminal position, only one $R_1$ is required, although others may be present.

In these formulas it should be recognized that each $N_{m1}Q_{m4}N_{m2}$ unit can differ from each other in a polynucleotide sequence in which m3 is greater than 1. That is, multiple Q moieties can be present randomly along the length of a molecule, provided that the remaining parameters described above are properly defined.

One group of suitable polynucleotides has a long sequence of uninterrupted normal bases with 1 to 5 Q moieties present at either or both ends of the molecule (e.g., 1 to 3 Q moieties). As noted, the Q moieties can be either consecutive or interrupted with a few normal nucleotides. Plural Q moieties (either consecutive or not) in the middle of a probe with relatively long uninterrupted sequences to either side of the crosslinking Q units also represent an embodiment of the invention.

In certain aspects of the invention, there is at least one uninterrupted sequence of nucleotides that is complementary to the corresponding target nucleotides. This uninterrupted sequence provides stability during the hybridization process so that proper recognition of the target will occur. The factors that lead to stability and selectivity are the same in the present process as in any other hybridization process. Uninterrupted sequences of complementary nucleotides followed by Q moieties are no different in this regard from uninterrupted sequences of target nucleotides followed by a non-complementary normal base. Thus, the stability of polynucleotides containing the crosslinking moiety of the invention can readily be predicted from standard considerations of nucleic acid hybridization.

Also suitable are compounds in which two $R_1$ groups are present in the B moiety and both represent a different hydroxyl-coupling or hydroxyl-protecting group, as such compounds are ready for use in the synthesis of a crosslinkable polynucleotide. These protecting and activating groups are also discussed elsewhere in this specification.

Another group of compounds of the invention have the formula II (shown below), many of which are within an embodiment of compounds of the scope encompassed by formula I:

(II)

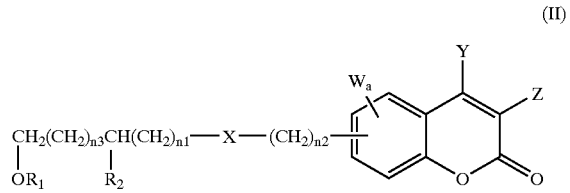

where n1 is 0 to about 10 (from about 0 to about 5, for example, from about 1 to about 3);

n2 is 0 to about 5 (from about 0 to about 2, for example, from about 0 to about 1);

n3 is from 0 to about 5 (from about 0 to about 2, for example, from about 0 to about 1);

each W is independently a small stable substituent containing up to 15 atoms (especially a lower hydrocarbyl group; a halo, nitro, thio, cyano, carbonyl, carboxy, hydroxy, amino, amido, or polyfluoroalkyl group; or a hydrocarbyl substituent containing one or more hetero atoms (i.e., an atom other than carbon or hydrogen that forms a stable covalent bond with carbon at 25° C. in water));

Y and Z independently represent H, F, or a lower alkyl group;

X is an organic group containing (a) from about 1 to about 10 carbon atoms and (b) from about 0 to about 10, for example, from about 0 to about 2, heteroatoms selected from the group consisting of O, S, and N, and wherein X comprises a shortest linking chain of from about 1 to about 10 atoms between the other atoms of the formula to which it is attached;

$R_2$ is H or $OR_1$; and $R_1$ is H or a group capable of coupling with or protecting (the former often being located only on a terminal hydroxyl of the backbone moiety) a hydroxy group during automated polynucleotide synthesis. Alternatively $R_1$ represents a nucleotide or polynucleotide linked to the compound by a phosphodiester linkage or other typical group used to couple sugars in polynucleotides. Suitable coupling groups include phosphorus-containing groups such as phosphite, phospohramidite, phosphate, H-phosphonate, phosphorothioate, phosphorodithioate, and methyl phosphonate. Non-phosphorus coupling groups include carbamates and amides. Lower hydrocarbon groups include $C_1$–$C_6$ alkenyl and alkenyl group as well as $C_3$–$C_6$ cyclic groups, and include $C_1$–$C_4$ alkyl and alkenyl groups, especially methyl, ethyl, propyl, isopropyl, butyl, isobutyl, sec-butyl, and tert-butyl. Typical hydrocarbyl groups with hetero atom substituents include —$COCH_3$, —$CH_2OH$, —$CF_3$, —$NHCH_3$, —$CO_2CH_2CH_3$, and —$CON(CH_3)_2$.

The hydroxyl(s) in the coumarin analogs of the invention can be protected (useful as coupling groups) by various protecting groups (P), such as those known in the art. An artisan skilled in the art can readily determine which protecting group(s) may be useful for the protection of the hydroxy group(s). Standard methods are known in the art and are more fully described in the literature. For example, suitable protecting groups can be selected by the skilled artisan, such as those described in Greene, T. W. W. and Wuts, P. G. "Protective Groups in Organic Synthesis," John Wiley & Sons, 1991, Chapters 5 and 7, the teachings of which are incorporated herein by reference. Exemplary protecting groups include those described throughout the specification.

Compounds of the invention are useful either as intermediates in the preparation of or as components of photoactive polynucleotides used, for example, as probes in hybridization assays. Since the intention is that one or more of these molecules eventually form part of a polynucleotide, the backbone moiety that forms part of the molecules is derived in most cases from either glycerin or a different polyhydroxy hydrocarbon molecule. The glyceryl or other polyhydroxy hydrocarbon moiety is incorporated at any position into the backbone of a nucleic acid typically by phosphodiester type linkage with the 3'- and/or 5'-hydroxy groups of the adjacent nucleotides in the molecule, with the crosslinking moiety normally being attached to the backbone moiety prior to such incorporation.

The crosslinking moiety portion of the compound of the invention can be derived from coumarin itself or any number of substituted coumarins. An organic functional group at the position in the crosslinking moiety precursor where a glyceryl or other backbone moiety will be attached is typically used to join the crosslinking moiety to the backbone moiety in the final product. Since final products can often be prepared by alternative synthetic routes, any given final product will likely have several possible precursors. The linking moiety can arise from a separate molecule or be formed by reaction between portions of the crosslinking moiety precursor and the backbone moiety precursor.

At locations other than the linking position, the coumarin (or other) ring system can be either unsubstituted or substituted. Typical substituents on the phenyl ring are small, stable substituents normally found on aromatic rings in organic compounds. Substituents can be selected as desired to change the excitation wavelength of the coumarin. Furthermore, the substituents can affect the thermal stability and the photo-reactivity of the compounds of the current invention. Substituents at the 3- and 4-positions are typically non-polar and are most often hydrocarbon substituents, with methyl substituents being most common. Although the location of coumarin substituents can vary, substituents are most often found at the 4-, 5-, 6-, 7-, and 8-positions.

In a certain embodiment, the coumarin moiety precursor, prior to reaction with the backbone moiety precursor, will have the formula:

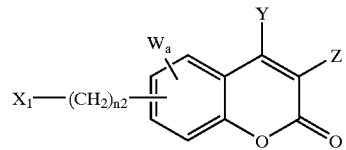

in which

W, Y, Z, and n2 have the meanings previously defined; and $X_1$ is a precursor of all or part of the X linking moiety, wherein $X_1$ will react with an organic functional group on the precursor of the linker moiety to form a covalent bond. Typical reactive functional groups include hydroxy, amine, halo, thio, carbonyl, carboxy ester, carboxy amide, silyl, and vinyl groups. These precursors can be synthesized by standard methods of organic synthesis from coumarin itself or from the many commercially available coumarin derivatives.

In certain embodiments the glycerol backbone moiety precursor has the formula:

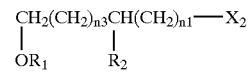

in which $R_1$, $R_2$, and n1, and n3 have the meaning previously defined; and $X_2$ is a precursor of all or part of the X linking group, wherein $X_2$ will react with an organic functional group on the coumarin moiety to form a covalent bond in the final linking X moiety. $X_2$ will typically be selected from reactive functional groups and nucleophilic and electrophilic groups that are capable of undergoing nucleophilic or electrophilic substitution or addition. Examples of specific functional groups include hydroxy, amino, halo, thio, carbonyl, carboxy ester, carboxy amide, vinyl, and silyl derivatives. This precursor can be synthesized by standard methods of organic synthesis from (poly)hydroxy hydrocarbons such as glycerin, commercially available 1,2- or 1,3-dihydroxy alkane derivatives, or such compounds with a protected hydroxy group at the location of the indicated hydroxy groups. See Misiura, K.; Durrant, I.; Evans, M. R.; and Gait, M. J. Nucleic Acids Res. (1990) 18, 4345–4354, which is herein incorporated by reference, for a discussion of attaching moieties having structures similar to those of the present backbone moieties to bases used in polynucleotide synthesis.

Compounds of the invention can be prepared by standard techniques of synthetic organic chemistry, using the guidelines outlined in this specification. For example, a typical synthesis based on commercially available starting materials is set forth in the following reaction scheme:

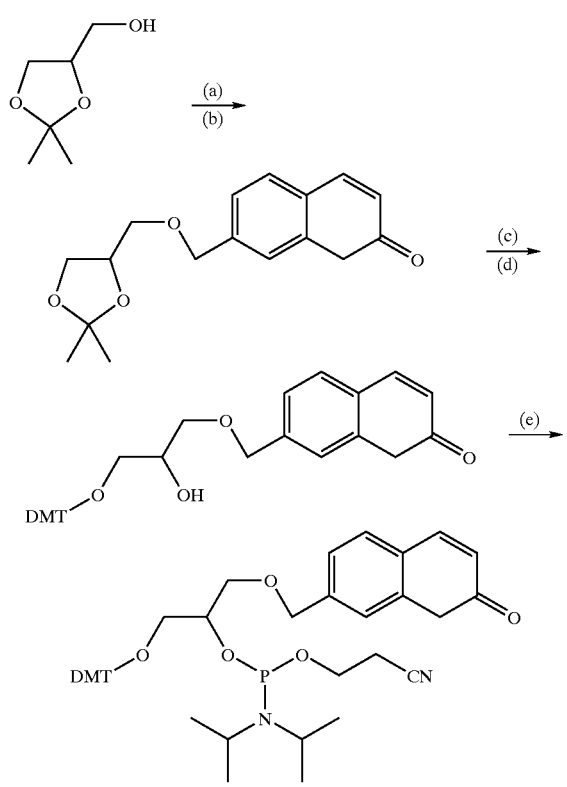

Reagents
(a) NaH/CH$_3$OCH$_2$CH$_2$OCH$_3$
(b) 7-bromomethylcoumarin
(c) HCl(aq), THF (tetrahydrofuran)
(d) DMTCl (4,4'-dimethoxytrityl chloride), pyridine
(e) 2-cyanoethyl diisopropylchlorophosphoramidite/
    diisopropylethylamine/dichloromethane

EXAMPLE 1
7-Coumarinylmethyl solketal

To 120 g ethylene glycol dimethyl ether was added solketal (2.64 g, 19.0 mmol) and sodium hydride (0.88 g, 22.0 mmol, 60% in mineral oil). To the resulting suspension was added 7-bromomethylcoumarin (4.8 g, 19.0 mmol) in small portions over a period of 7 min. After 10 min, 1.5 mL glacial acetic acid was added to stop the reaction. The solid was then separated from the resulting suspension by centrifugation. The solution was then concentrated to a solid. This solid was purified by silica gel chromatography using chloroform:ethyl acetate (97:3) as the eluant. The fractions containing product were identified by TLC and were combined and concentrated to a white solid in vacuo. Yield: 630 mg; melting point: 75–80° C.; $R_f$=0.55 (chloroform:ethyl acetate (9:1)).

EXAMPLE 2
1-O-(4,4'-Dimethoxytrityl)-3-O-(7-coumarinylmethyl) glycerol

7-Coumarinylmethyl solketal (800 mg, 2.74 mmol) was dissolved in a solution of tetrahydrofuran (12 mL) and hydrochloric acid (6 mL) for 20 min. The solution was then dried by co-evaporation with absolute ethanol (2×5 mL) to give an oil. The resulting solution was washed with 25 mL saturated sodium carbonate and then extracted with 3×25 mL diethyl ether. The solution was concentrated to an oil in vacuo. The oil was dried by co-evaporation with pyridine (2×5 mL) to give a dry product. To the liquid was added pyridine (30 mL), 4-dimethylaminopyridine (25 mg) and triethylamine (200 μL). To the resulting solution was added 4,4'-dimethoxytrityl chloride (905 mg, 2.95 mmol). The reaction mixture was stirred for two hours. 37.5 mL water was added to stop the reaction, and the resulting solution was extracted with 2×180 mL diethyl ether. The combined ether extracts were concentrated in vacuo, dissolved in 15 mL methylene chloride, and purified by silica gel chromatography using acetone:hexane (4:6) as the elution solvent. Fractions with $R_f$=0.5 were collected and evaporated to dryness to yield the product (770 mg, 55% yield).

EXAMPLE 3
1-O-(4,4'-Dimethoxytrityl)-3-O-(7-coumarinylmethyl)-2-O-(2-cyanoethyl diisopropylphosphoramidite)glycerol 1-O-(4,4'-Dimethoxytrityl)-3-O-(7-coumarinylmethyl) glycerol (1.20 g, 2.18 mmol) was co-evaporated twice with 2×6.5 mL mixed solution of 5 mL pyridine and 1.5 mL methylene chloride. To the dry reactant was added methylene chloride (4.6 mL) and diisopropylethylamine (1.87 mL, 8.59 mmol). The suspension was stirred until it became a clear solution. Then, 2-cyanoethyl diisopropylchlorophosphoramidite (0.62 ml, 3.24 mmol) was added to the solution. The resulting solution was stirred for 65 min. The reaction mixture was then diluted with 45 mL ethyl acetate and 2.2 mL triethylamine, extracted with 10% aqueous sodium carbonate (2×30 mL), and with saturated sodium carbonate (2×30 mL), and with saturated sodium chloride (2×30 mL). The organic phase was concentrated in vacuo. The resulting product was purified by silica gel chromatography with a methylene chloride:diethyl ether:triethylamine (90:7.5:1) solvent system. Fractions with $R_f$=0.73 were collected. The product was concentrated in vacuo to a solid. Yield: 1.06 g (1.41 mmol, 64%).

EXAMPLE 4

Preparation of Oligodeoxynucleotides Containing a Non-Nucleosidic Coumarin Functionality Using the reagent prepared in Example 3, above, an oligonucleotide was prepared via the β-cyanoethylphosphoramidite method of DNA synthesis that was identical to a segment of human papilloma virus type 16, comprising nucleotides 397 to 417 of the E6 gene in which the 20th base (adenine) was replaced by 3-(7-coumarinylmethyl) glycerol.

After assembly, the oligonucleotide was cleaved from the solid support with 3 mL 30% NH$_4$OH for 1.5 hr at room temperature. The ammonia solution was then heated at 55° C. for 1.5 hr. After cooling, the NH$_4$OH was removed in vacuo. The crude oligonucleotide was purified to homogeneity by reversed-phase high performance liquid chromatography (HPLC).

The oligonucleotide was hybridized in 0.75 M NaCl buffer (20 μL) with a complementary 5'-$^{32}$P-labeled target oligonucleotide (molar ratio of probe:target=10:1) for 1 hr at 40° C. At this time the solution was irradiated with 302 nm wavelength light for 10 min. Denaturing polyacrylamide gel electrophoresis analysis of the irradiated mixture indicated that the level of photochemical crosslinking achieved with respect to the radiolabeled target was 80%. Control experiments with analogous oligonucleotides containing one of the nucteosidic coumarin derivatives described in Saba et al., U.S. Pat. No. 5,082,934, were carried out in parallel. The optimal crosslinking efficiencies obtained with these reagents were 60%. Accordingly, the compound of the invention underwent photochemical crosslinking with 20% more efficiency (⅓ greater relative efficiency).

EXAMPLE 5

By following a similar reaction shown in the previous examples 1, 2, and 3, a product could also be synthesized with the following structure:

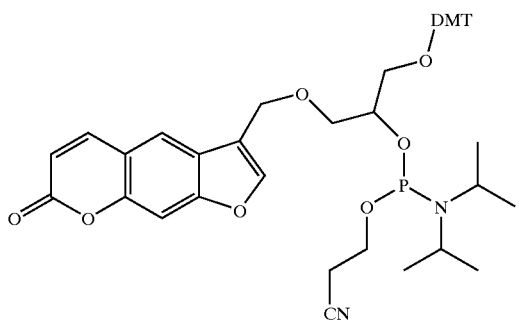

This compound would be also useful for the preparation of oligodeoxynu-cleotides containing non-nucleotide psoralen derivatives.

EXAMPLE 6

Using the reagent prepared in Example 3, oligonucleotides were prepared via the β-cyanoethylphosphoramidite method of DNA synthesis that were identical to segments of the genome of human papilloma virus type 16, The oligonucleotides were complementary to nucleotides 89–108 and 283–302 of the E6 gene, respectively (the sequence of which is herein incorporated by reference). In each molecule, the 5'-terminal nucleotide of the natural sequence (adenosine) was replaced by 3-(7-coumarinylmethyl) glycerol. The 3'-end terminated with a biotin moiety.

In parallel, two additional DNA molecules were synthesized. These oligonucleotides had sequences complementary to either nucleotides 89–108 or 283–302 of the E6 gene; however, in these modified oligonucleotides 3-(7-coumarinylmethyl) glycerol was replaced by the nucleosidic coumarin derivative described in Saba et al., U.S. Pat. No. 5,082,934, by using the 3'-O-(N,N-diisopropyl phosphoramidite) 5'-O-(4,4'-dimethoxytrityl) derivative at the 5'-position of the 2'-deoxyribonucleotide, herein referred to as the "Saba compound."

After assembly, the four oligonucleotides were cleaved from the solid support with 1 mL 30% $NH_4OH$ for 1.5 hr at room temperature. The ammonia solution was then heated at 55° C. for a further 1.5 hr. After cooling, the $NH_4OH$ was removed in vacuo. The crude oligonucleotides were purified to homogeneity by HPLC.

The oligonucleotides were hybridized in 0.75 M NaCl buffer (20 μL) with complementary 5'-$^{32}$P-labeled oligonucleotides (molar ratio of unlabeled:labeled oligonucletides=100:1) for 1 hr at 40° C. At this time the solutions were irradiated with UV-B wavelength light (XL-1500 UV crosslinker, Spectronics) for 15 min. The extent of crosslinking (with respect to the radiolabeled targets) was determined by denaturing polyacrylamide gel electrophoresis followed by scintillation counting of the excised bands. The results are set forth in the following table:

| E6 Gene Sequence | Crosslinker Used in | Crosslinking Reaction Site | Crosslinking Efficiency |
|---|---|---|---|
| 89-108 | 3-(7-Courmarinylmethyl) glycerol | TTT | 64 |
| 89-108 | Saba compound | TTT | 54 |
| 283-302 | 3-(7-Courmarinylmethyl) glycerol | TTT | 76 |
| 283-302 | Saba compound | TTT | 68 |

The results indicate that the compounds of the current invention undergo photochemical crosslinking more efficiently than the compound of U.S. Pat. No. 5,082,934 (>10% greater relative efficiency).

EXAMPLE 7

1-O-(4,4'-Dimethoxytrityl)-3-O-(7-coumarinyl)-2-O-(2-cyanoethyl diisopropylphosphoramidite)glycerol Another embodiment of the invention was synthesized using 7-hydroxycoumarin instead of 7-bromomethylcoumarin as in Example 1, The reaction scheme for the synthesis of 1-O-(4,4'-dimethoxytrityl)-3-O-(7-coumarinyl)-2-O-(2-cyanoethyl diisopropylphosphoramidite) glycerol is as follows:

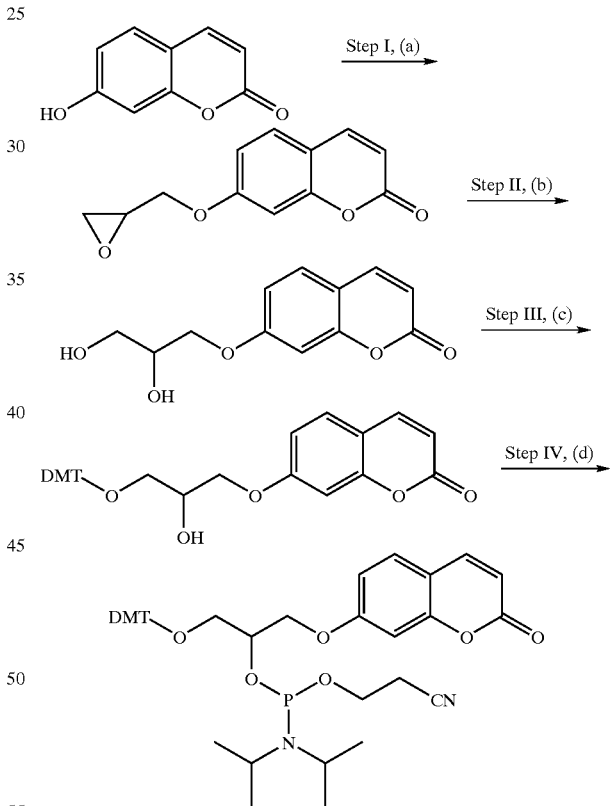

Reagents
(a) epibromohydrin/potassium carbonate/acetone
(b) $H_2SO_4$(aq)/acetone
(c) DMTCl (4, 4'-dimethoxytrityl chloride), pyridine This synthetic route requires less time to complete than the reaction sequence using 7-bromomethylcoumarin and provides a cost savings of about 50 percent compared to the 7-bromomethylcoumarin synthetic sequence. The 7-hydroxycoumarin derivatives can be introduced into oligonucleotides and are more stable during deprotection of the oligonucleotides (exposure to concentrated $NH_3$ at room temperature) than compounds of U.S. Pat. No. 5,082,934.

The 7-hydroxycoumarin derivatives exhibit a different absorption spectrum (λ maximum of 325 nm) compared to the 7-bromomethylcoumarin derivatives (λ maximum of 310 nm). The 7-hydroxycoumarin derivatives are red-shifted relative to the 7-bromomethylcoumarin derivatives, which reduces the effect of quenchers, such as nucleic acids. The spectral shift also allows for more selective excitation of the 7-hydroxycoumarin derivatives.

Synthesis of 7-glycidylcoumarin (Step I)

The intermediate 7-glycidylcoumarin was prepared in a reaction flask equipped with a reflux condenser containing 16.2 g 7-hydroxycoumarin, 15.8 g epibromohydrin, 13.8 g potassium carbonate and 270 mL acetone. The reaction solution was boiled and refluxed overnight, cooled, treated with 100 mL 5% NaOH aqueous solution, and extracted three times with 80 mL methylene chloride. After evaporating the solvent, a crude yellow solid was obtained. The crude solid (1.5 g) was dissolved in a solution of 30 mL hexane and 20 mL acetone at 50° C. The hexane/acetone solution was then cooled at 0° C. for 2 to 3 hr. White crystals formed and were collected by filtering and dried to a white powder. Yield: 290 mg; melting point: 110–112° C.; $R_f$=0.6 (8% v/v ethyl acetate/$CHCl_3$).

Hydrolysis of 7-glycidylcoumarin (Step II)

7-Glycidylcoumarin (2.0 g) was dissolved in a solution of 80 mL acetone and 50 mL of 1.8 M $H_2SO_4$. The acetone/acid solution was heated to a boil for 20 min. The solution was cooled and neutralized with a 1.6 M $NH_4OH$ until a pH of 7–8 was reached. The neutralized solution was extracted with 50 mL ethyl acetate three times. After evaporating the solvent, the product, 7-(1-O-glyceryloxy)coumarin, was obtained with a melting point of 118–120° C.

Synthesis of 1-O-(4,4'-dimethoxytrityl)-3-O-(7-coumarinyl) glycerol (Step III)

Coumarinyl glycerol (1.37 g) was co-evaporated with 11 mL of purified pyridine by rotary evaporation three times. The co-evaporated coumarinyl glycerol was combined with 44 mg 4-dimethylaminopyridine, 330 μL triethylamine, 45 mL pyridine, and 1.78 g dimethoxytrityl chloride. The solution was stirred at room temperature for 3 hr. The reaction was stopped by adding 66 mL deionized water. The reaction solution was then extracted three times with 35 mL methylene chloride. The organic phase was dried over sodium sulfate. The crude product obtained by evaporating the solvent was purified by chromatography using a silica gel column and eluting with a solution of hexane:acetone:triethylamine (70:28:2). Yield: 2.6 g; $R_f$=0.43 (hexane:acetone:triethylamine (70:28:2)).

Synthesis of 1-O-(4,4'-dimethoxytrityl)-3-O-(7-coumarinyl)-2-O-(2-cyanoethyl-N,N-diisopropyl Phosphoramidite)glycerol (Step IV)

1-O-4,4'-Dimethoxytrityl-3-O-(7-coumarinyl) glycerol (2.5 g) was co-evaporated with 12 mL pyridine:methylene chloride (75:25) two times. A solution of 5 mL methylene chloride and 5 mL pyridine was added to the dry viscous liquid. This solution was added under argon to a 50 mL flask containing a solution of 3 mL diisopropylethylamine, 10 mL methylene chloride, and 1.8 g 2-cyanoethyl diisopropylchlorophosphoramidite. The solution was stirred for 90 min. The reaction mixture was diluted with a solution of 60 mL ethyl acetate and 3 mL triethylamine. The reaction mixture was extracted two times with 50 mL saturated sodium chloride. The organic phase was then dried over sodium sulfate. The crude product was purified by a silica gel chromatography column. Yield: 2.6 g; $R_f$=0.2 (hexane:acetone (80:20)).

EXAMPLE 8

Using the reagent prepared in Example 7, oligonucleotides were prepared via the β-cyanoethylphosphoramidite method of DNA synthesis that were identical to segments of the cryptic plasmid of Chlanydia trachomatis. The oligonucleotides were complementary to nucleotides 876–900, 6857–6878, 7118–7140, and 6725–6752 of the cryptic plasmid (the sequence of which is herein incorporated by reference), the first two oligonucleotides containing one crosslinking compound per oligonucleotide and the latter two oligonucleotides containing two crosslinking compounds per oligonucleotide.

After automated synthesis, the oligonucleotides were cleaved from the solid support and deprotected with 3 mL 30% $NH_4OH$ for 2 hr at room temperature. The $NH_4OH$ was removed in vacuo, and the crude oligonucleotide was purified to homogeneity by denaturing polyacrylamide gel electrophoresis.

The oligonucleotides were hybridized in 0.75 M NaCl buffer (195 μL) with complementary 5'-$^{32}$P-labeled oligonucleotides (molar ratio of unlabeled:labeled oligonucleotides=100:1) for 20 min at 40° C., at which time the solutions were irradiated with UV-A wavelength light (8 W lamp) for 20 min. The extent of crosslinking (with respect to the radiolabeled oligonucleotide) was determined by denaturing polyacrylamide gel electrophoresis followed by scintillation counting of the excised bands. The results are set forth in the following table:

| Cryptic Plasmid of Chlamydia trachomatis | Number of Crosslinkers in Oligonucleotide | Crosslinking Reaction Site(s) (5' □ 3') | Crosslinking Efficiency (%) |
|---|---|---|---|
| 876-900 | 1 | TTA | 88 |
| 6857-6878 | 1 | TTT | 86 |
| 7118-7140 | 2 | TTT, TAT | 99 |
| 6725-6752 | 2 | TAC, TTT | 98 |

The results indicate that the compounds of the current invention undergo photochemical crosslinking more efficiently than the compound of U.S. Pat. No. 5,082,934.

EXAMPLE 9

Coumarin derivatives can be synthesized containing various side chains, including, (1) short side chains, such as glycerol, (2) long side chains, such as poly(ethylene glycol)s, (3) aromatic rings, and (4) aliphatic cyclic rings, such as ethylene-dioxy rings. Such coumarin derivatives can be synthesized from the appropriate coumarin starting materials, such as, 7-methylcoumarin, 7-hydroxycoumarin, esculetin (6,7-dihydroxycoumarin), and 7-glycidylcoumarin. Attached to each coumarin starting material is the desired side chain containing active functional groups.

Reaction Scheme for a Coumarin Containing an Aliphatic Heterocyclic Ring Derivative 1-O-(2-cyanoethyl diispropylphosphoramidite)-2,3-O-(6,7-coumarinyl)glycerol This compound is not itself a compound within the general formulas described above, but is an intermediate that can be used to prepare such compounds via reaction of X and/or B unit precursors with the hydroxy group that is activated by formation of a phosphoramidite in the last step of the following reaction:

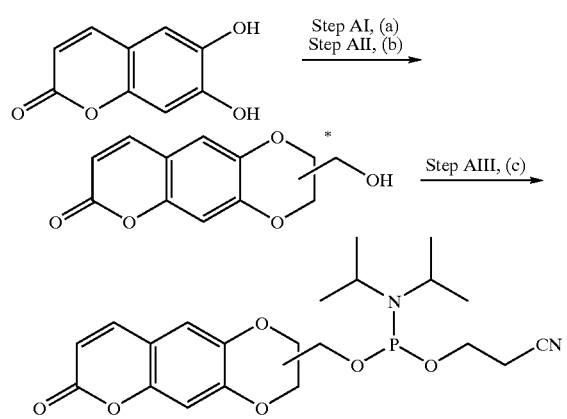

Reagents
(a) epibromohydrin/potassium carbonate/acetone
(b) potassium hydroxide
(c) 2-cyanoethy diisopropychlorophosphoramidote/
   diisopropylethylamine/pyridine/dichloromethane

*mixture of:

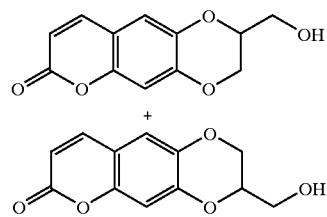

Reaction at Step AI with 2,3-dibromo-1,4-dihydroxybutane instead of epibromohydrin gives the compound 2-O-,3-O-(6,7-coumarinyl) 1,2,3,4-tetrahydroxy-butane. This compound can then be converted to 1-O-(4,4'-dimethoxytrityl)-4-O-(2-cyanoethyl diisopropylphosphoramidite)-2-O-,3-O-(6,7-coumarinyl) 1,2,3,4-tetrahydroxy-butane, shown below:

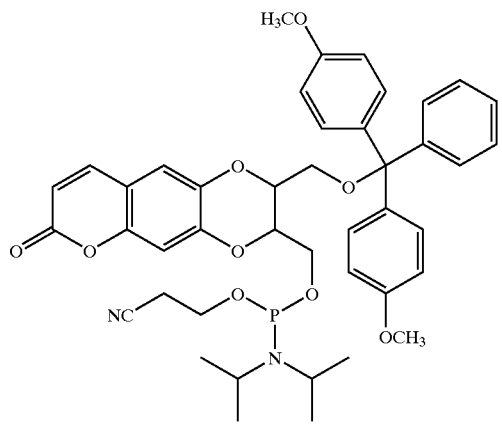

Preparation of 6,7-(hydroxymethylethylenedioxy)coumarin (Steps AI and AII).

Esculetin (0.90 g) was stirred with a solution of potassium carbonate (1.40 g) and 200 mL anhydrous acetone for 1 hr at room temperature. Epibromohydrin (1.05 g) was added to the solution. The yellow suspension was then refluxed overnight. Potassium hydroxide (0.70 g) was added and refluxed for one hour. The solution was then separated from the solids by centrifugation. The resulting solution was evaporated by a water aspirator. The resulting product was then dissolved in 50 mL water. The aqueous solution was extracted three times with 35 mL methylene chloride. The organic solution was extracted twice with 50 mL 2 M sodium hydroxide. The resulting organic phase was dried over sodium sulfate. After evaporating the solvent, 200 mg of product was obtained as white solid. Yield: 26%; $R_f$=0.42 (acetone:hexane (1:1)).

Preparation of Aliphatic Heterocyclic Ring Derivative (Step AIII)

6,7-(Hydroxymethylethylenedioxy)coumarin (200 mg) was co-evaporated with 1 mL dry pyridine, twice. To the dry reactant, 0.9 mL dichloromethane and 0.9 mL pyridine was added. 2-Cyanoethyl diisopropylchlorophosphoramidite (280 mg) was dissolved in a solution of 0.2 mL diisopropylethylamine and 0.9 mL dichloromethane. The phosphoramidite solution was added to the coumarin solution. The resulting solution was stirred at room temperature for 2 hr. The reaction mixture was then diluted with a solution of 10 mL ethyl acetate and 0.5 mL triethylamine. The solution was extracted three times with 6 mL saturated sodium chloride solution. After evaporation of the solvent, the resulting product was purified by a silica gel column with acetone::hexane:triethylamine (36:60:4). The purified product (100 mg) was obtained with an $R_f$=0.57 (acetone:hexane:triethylamine (36:60:4)).

Reaction Scheme for a Coumarin Connected to an Aromatic Side Chain

3-O-(7-Coumarinylmethoxy)-1-O-(2-cyanoethyl diisopropyl phosphoramidite) 1,3-dihy-droxybenzene

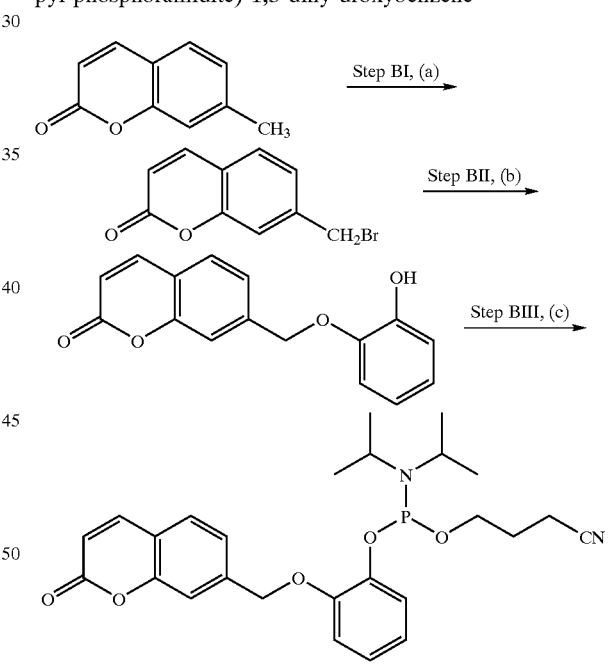

Reagents
(a) N-bromosuccinimide/chloroform
(b) resorcinol/potassium carbonate/acetone
(c) 2-cyanoethyl diisopropylchlorophosphoramidite/
   diisopropylethylamine/pyridine/dichloromethane Preparation of 7-bromomethylcoumarin (Step BI)

7-Methylcoumarin (28 g), 70% benzoylperoxide (1.68 g), and N-bromosuccinimide (30.8 g) was added to 140 mL chloroform in a one liter flask, and the suspension was refluxed overnight. The solution was diluted with 100 mL chloroform. The resulting crude product was recrystallized from 750 mL acetone. A white solid (21 g) with a melting point of 172–176° C. was obtained.

Preparation of 3-O-(7-coumarinylmethyl) 1,3-dihydroxybenzene (Step BII)

7-Bromomethylcoumarin (0.70 g) was added to a suspension of resorcinol (2.25 g), potassium carbonate (1.75 g), and acetone (200 mL). The solution was heated and stirred for 4 hr. The solution was then separated from the solid. After evaporating the solvent, the crude product was dissolved in 40 mL dichloromethane. The organic solution was then extracted three times with 40 mL water. TLC using 20% (v/v) ethyl acetate/chloroform gave $R_f=0.32$. After evaporating the solvent, the product was recrystallized from $CH_2Cl_2$/ethyl acetate, yielding 300 mg of purified product.

Preparation of 3O-(7-coumarinylmethoxy)-1-O-(2-cyanoethyl diisopropylphosphoramidite) 1,3-dihydroxybenzene (Step BIII)

2-cyanoethyl diisopropylchlorophosphoramidite was reacted with the product of Step BII in a fashion similar to that of Step AIII.

Reaction Scheme for a Coumarin Containing a Long Side Chain

3-O-(7-Coumarinyl)-2-O-(2-cyanoethyl diisoprophylphosphoramidite)-1-O-(2-[2-(4,4'-dimethoxytrityloxy)ethoxy]ethyl)glycerol

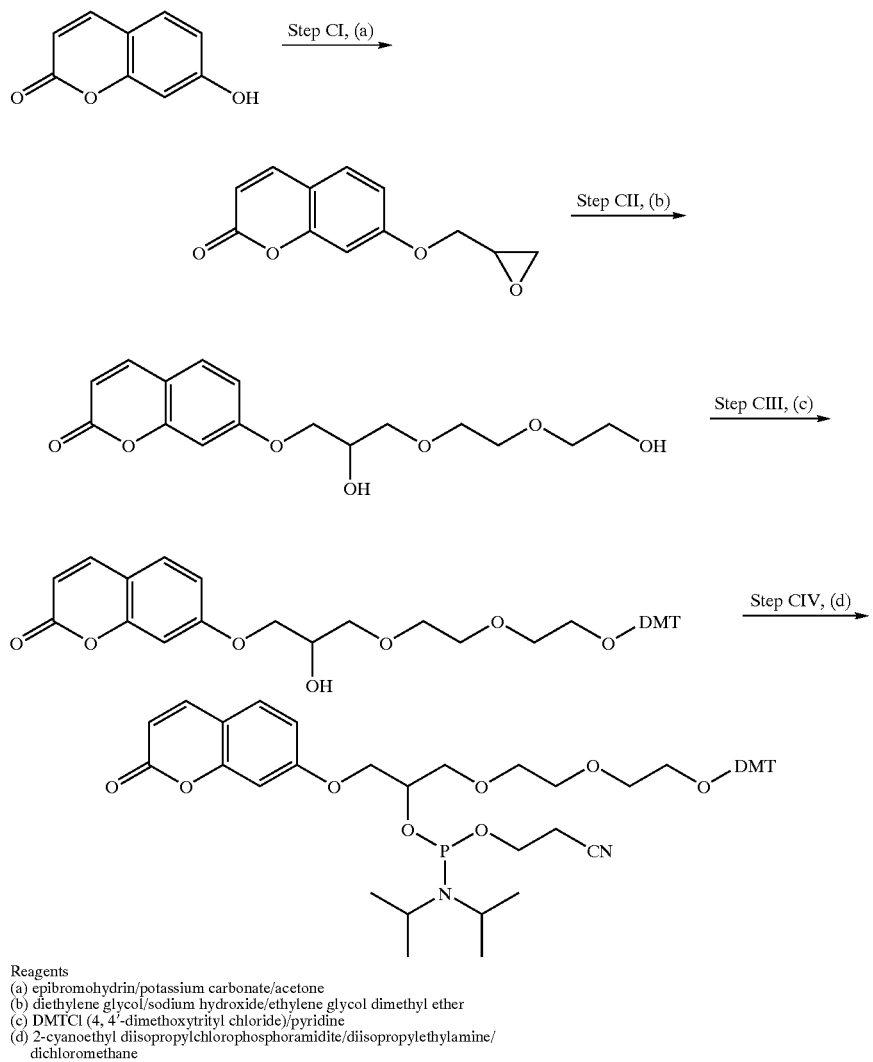

Reagents
(a) epibromohydrin/potassium carbonate/acetone
(b) diethylene glycol/sodium hydroxide/ethylene glycol dimethyl ether
(c) DMTCl (4, 4'-dimethoxytrityl chloride)/pyridine
(d) 2-cyanoethyl diisopropylchlorophosphoramidite/diisopropylethylamine/ dichloromethane Preparation of 7-glycidylcoumarin (Step CI)

7-Glycidylcoumarin was prepared as described in Step 1 of Example 7.

Preparation of 3-O-(7-coumarinyl)-1-O-(2-[2-hydroxyethoxy]ethyl)glycerol (Step CII)

7-Glycidylcoumarin (1 g) was dissolved in a solution of 10 mg sodium hydroxide, 2.65 g diethylene glycol, and 5 mL ethylene glycol dimethyl ether. The solution was heated to reflux for 6 hr. The reaction mixture was diluted with 10 mL de-ionized water and was extracted three times with 10 mL dichloromethane. The organic phase was then dried over sodium sulfate. After evaporating the solvent, the crude product was purified by a silica gel chromatography using 50% (v/v) acetone/hexane. A major product with $R_f=0.09$ (260 mg) and a minor product with $R_f=0.34$ (50 mg) (50% (v/v) hexane/acetone) were obtained.

Preparation of 3-O-(7-coumarinyl)-1-O-(2-[2-(4,4'-dimethoxytrityloxy)ethoxy]ethyl)glycerol (Step CIII)

The dihydroxy coumarin derivative (230 mg) obtained as the product of Step CII was co-evaporated with dry pyridine. 4,4'-Dimethoxytritylchloride (320 mg), 60 mL triethylarnine, and 10 mg 4-dimethylaminopyridine were added to the coumarin derivative. The solution was stirred at room temperature for 16 hr. The solution was diluted with water and extracted with dichloromethane, then dried with sodium sulfate. After evaporating the solvent, the crude product was purified by a silica gel chromatography using 40% (v/v) acetone/hexane.

Preparation of 3-O-(7-coumarinyl)-2-O-(2-cyanoethyl diisopropylphosphoramidite)-1-O-(2-[2-(4,4-dimethoxytrityloxy)ethoxy]ethyl)glycerol (Step CIV)

2-Cyanoethyl diisopropylchlorophosphoramidite was reacted with the product of Step CIII as described in Step AIII.

Preparation of Phosphoramidites in Steps AIII, BIII, and CIV

The general procedure for preparing the phosphoramidite is as follows. Under an inert atmosphere 1.2 equiv 2-cyanoethyl diisopropylchlorophosphoramidite and 2.4 equiv diisopropylethylamine are dissolved in 0.9 mL dichloromethane in a glass container capped with a septum. The coumarin precursor (1.0 equiv) (such as the product of Step AII, BII, or CIII) was dissolved 9.9 mL pyridine and 0.9 mL dichloromethane. While the chlorophosphoramidite solution is stirred, the coumarin solution is added. Stirring is continued for 2 hr. Ethyl acetate is added, and the organic solution is washed with NaCl (aqueous) three times and dried with $Na_2SO_4$. After removing the solvent, the crude product is purified by column chromatography using acetone:hexane:triethylamine (36:60:4). Appropriate fractions are collected and concentrated under vacuum.

EXAMPLE 10

Synthesis of an Oligonucleotide Containing the XL3 Crosslinker and HPLC Purification of the Probe into Two Isomeric Form The formula for XL3 is:

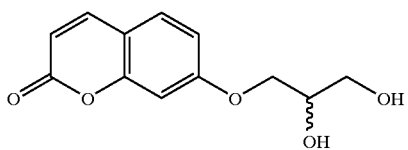

An oligonucleotide, NAX523, containing the XL3 moiety was synthesized using standard DNA synthesis techniques:

NAX523: 3'-AAA A(XL3)A CAT ACA CCT TAC AGC TT-5' (SEQ ID NO: 1).

The oligonucleotide was analyzed by reversed-phase HPLC using a C8-Porex column (Phenomenex). The elution gradient for the column was 0.1 M triethylamine acetate (pH 7.0) to 22.5% acetonitrile in 0.1 M triethylamine acetate (pH 7.0) over 45 min at a flow rate of 1 mL/min. The column eluate was monitored using a UV detector set at 260 um.

Analysis showed that the oligonucleotide eluted as 2 distinct peaks of equal size at 34 min (isomer #1) and 35 min (isomer #2). The molecules leading to these peaks were purified by collecting the column eluate at the time the peaks appeared.

EXAMPLE 11

Crosslinking Analysis of an Oligonucleotide Containing XL3 and Two HPLC-Purified Isomers of the Oligonucleotide An oligonucleotide target that was complementary to NAX523 was synthesized and labeled at the 5'-end with $^{32}p$.

The $^{32}$P-labeled oligonucleotide (0.4–0.5 pmol) was added to three tubes that contained at least a 10-fold molar excess of either NAX523 or one of the two HPLC-purified oligonucleotide isomers from Example 10. The final volume in each tube was then made up to 0.2 mL by the addition of formamide and NaCl solutions to give final Na+ and formamide concentrations of 0.75 M and 21.5% (v/v), respectively.

The contents of each tube were transferred to individual wells of a 96-well microtiter plate and heated to 40° C. The samples were then irradiated for up to 600 s using 350 nm UV lamps in a UV light box (UVP). The lamps were situated ~2.5 cm from the samples. Aliquots (10 µL) of the reaction mixtures were removed at 30, 60, 300, and 600 s.

Upon completion of the reactions, the products were electrophoresed through 15% polyacrylamide gels containing 7 M urea, and the gel was exposed to X-ray film overnight. Analysis of the film indicated that the $^{32}$P-labeled target in each lane migrated through the gel to form two distinct bands. The relative proportions of the two bands depended on the irradiation time. The amount of the faster moving band (unreacted target) decreased upon increased irradiation time whereas the slower moving band (crosslinked target) increased.

The amount of crosslinked product formed at each time point was quantified by cutting out the radioactive bands from the gel and counting them in a scintillation counter. The following results were obtained for the three reactions:

|  | Crosslinking (%) | | |
| --- | --- | --- | --- |
| UV Irradiation (s) | NAX523 | NAX523 (isomer #1) | NAX523 (isomer #2) |
| 30 | 22.8 | 16.0 | 35.4 |
| 60 | 41.3 | 30.4 | 60.3 |
| 300 | 79.6 | 70.5 | 92.7 |
| 600 | 83.0 | 73.3 | 95.2 |

The data showed that the two purified isomers reacted at significantly different rates to each another. At the earliest time point investigated (30 s), NAX523 (isomer #2, XL10) had reacted with the target to yield over twice as much crosslinked product as NAX523 (isomer #1, XL9) and over 1.5-fold more than the XL3-modified oligonucleotide, NAX523.

EXAMPLE 12

Synthesis of Oligonucleotides Containing XL9 and XL10 Crosslinkers and HPLC Analysis of the Oligonucleotides The formula for XL9 is:

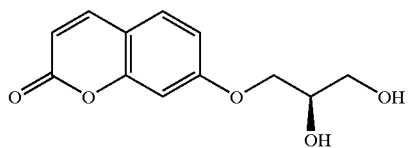

The formula for XL10 is:

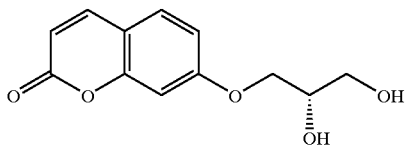

The XL3 crosslinker is a racemic mixture of two optical isomers, XL9 and XL10. Two oligonucleotides, NAX622 and NAX623, containing either the XL9 or XL10 moiety, respectively, were synthesized using standard DNA techniques:

NAX622: 3'-AAA A(XL9)A CAT ACA CCT TAC AGC TT-5' (SEQ ID NO: 1)).

NAX623: 3'-AAA A(XL10)A CAT ACA CCT TAC AGC TT-5' (SEQ ID NO:1).

The probes were analyzed using the same HPLC conditions as described in Example 10. Both oligonucleotides eluted from the column as single peaks. Co-injection of the XL9-containing oligonucleotide, NAX622, with the XL3 oligonucleotide of the same sequence, NAX523, showed that NAX622 co-eluted with the first peak of NAX523. Co-injection of the XL10-containing oligonucleotide, NAX623, with NAX523 showed that NAX622 co-eluted with the second peak of NAX523.

These data indicate that the NAX523 probe is composed of two separable diastereoisomers that contain either XL9 or XL10. The crosslinking analysis described in Example 11 shows that an oligonucleotide containing XL10 reacts significantly faster than an oligonucleotide containing XL3, which in turn reacts faster than an oligonucleotide containing XL9.

Preparation of XL10

(2S)-Glycidyl 7-coumarinyl ether

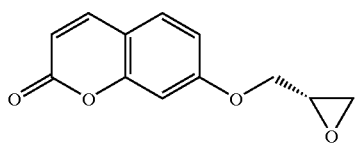

(III)

650 mg (4.0 mmol) 7-hydroxycoumarin and 622 mg potassium carbonate were dissolved in a solvent mixture composed of 40 mL acetone and 80 mL dry dimethylformamide. The resulting solution was heated at 50–60° C. for 1 hr with stirring. To this solution was added 910 mg (3.5 mmol) (2S)-(+)-glycidyl 3-nitrobenzenesulfonate. This solution was heated at 60–70° C. for 30 min, after which it was stirred overnight at room temperature. The solution was then heated at 60–70° C. for an additional 2 hr. The solvent was removed from the reaction mixture by rotary evaporation. To the resulting residue was added 30 mL ethyl acetate. This solution was extracted with 4×15 mL 1% sodium hydroxide followed by 2×15 mL 1% sodium chloride. The organic phase was dried over sodium sulfate. After filtration and solvent evaporation, approximately 1 g crude product was isolated as a wet yellow solid. This material was purified by silica gel chromatography using acetone:hexane (25:75 to 45:55). 420 mg (55% yield) product was obtained as a white solid.

(2S)-1-O-(7-Coumarinyl)glycerol (XL10)

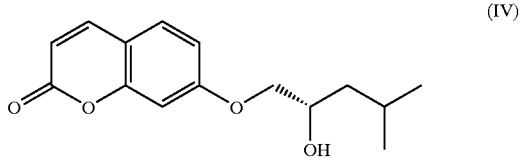

(IV)

400 mg (1.8 mmol) compound III was dissolved in 16 mL acetone. To this solution was added 8 mL 2 M sulfuric acid. The resulting solution was heated at 55–60° C. for 1 hr with stirring. The acetone was removed from the reaction mixture by rotary evaporation. The remaining aqueous solution was neutralized to pH 7 by the addition of 10% sodium hydroxide. The neutralized solution was extracted with 4×20 mL ethyl acetate. Evaporation of the ethyl acetate yielded 415 mg (98% yield) product as a white solid.

(2S)-1-O-(7-Coumarinyl)-3-O-(4,4'-dimethoxytrityl) glycerol

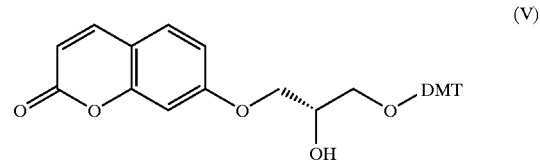

(V)

320 mg (1.4 mmol) compound IV was dried by the addition of 2 mL pyridine followed by evaporation under vacuum. This drying procedure was repeated once. To the resulting solid was added 12 mg N,N-dimethylaminopyridine, 96 μL triethylamine, 480 mg (1.4 mmol) 4,4'-dimethoxytrityl chloride (DMTCl), and 11 mL pyridine. The resulting solution was stirred at room temperature for 70 min. To this solution was added 50 mL methylene chloride containing 2% triethylanine. The solution was extracted with 3×15 mL saturated sodium chloride. The combined organic phase was dried over sodium sulfate. After filtration and solvent evaporation, crude product was obtained as a viscous liquid. This material was purified by silica gel chromatography using acetone:hexane:triethylamine (25:75:3) to yield approximately 550 mg (73% yield) product.

(2S)-1-O-(7-Coumarinyl)-2-O-(2-cyanoethyl diisopropylphosphoramidite)-3-O-(4,4'-dimethoxytrityl) glycerol

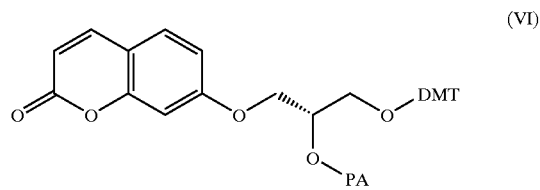

(VI)

400 mg (0.74 mmol) compound V was dried by the addition of 2 mL pyridine followed by evaporation under vacuum. To the resulting solid was added under a dry argon atmosphere a solution containing 500 μL diisopropylethylamine in 2 mL methylene chloride. This solution was then added to a solution containing 500 μL (2.2 mmol) 2-cyanoethyl diisopropylchlorophosphoramidite (PACl) and 500 μL diisopropylethylamine in 2 mL methylene chloride.

This solution was stirred at room temperature of 1 hr. The reaction was diluted with methylene chloride containing 5% triethylamine. The resulting solution was extracted with 4×20 mL saturated sodium chloride. The organic phase was evaporated to isolate crude product. This material was purified by silica gel chromatography using acetone:hexane:triethylamine (20:80:3) to yield approximately 400 mg (73% yield) product.

Preparation of XL9

XL9, the enantiomer of XL10, was prepared by using (2R)-(−)-glycidyl 3-nitrobenzenesulfonate in the first step of the synthetic procedure described in this example.

EXAMPLE 13

Crosslinking Analysis of Oligonucleotides Containing XL51, XL52, and XL53

The XL51 crosslinker, having the structure:

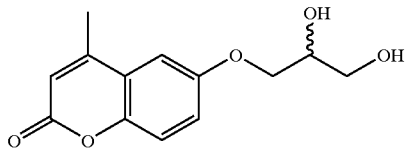

is a racemic mixture of two optical isomers, XL52 and XL53. The structure for XL52 is:

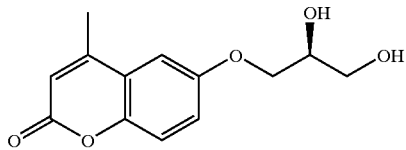

and the structure for XL53 is:

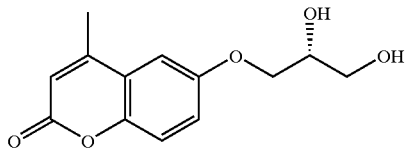

Three oligonucleotides, NAX3220, NAX3272, and NAX3273 containing either the XL51, XL52, or XL53 moiety, respectively, were synthesized using standard DNA synthesis techniques:

NAX3220: 3'-TAA AAC AGA AAC GCG TAC CGA (XL51)A-5' (SEQ ID NO:2).

NAX3272: 3'-TAA AAC AGA AAC GCG TAC CGA (XL52)A-5' (SEQ ID NO:2).

NAX3273: 3'-TAA AAC AGA AAC GCG TAC CGA (XL53)A-5' (SEQ ID NO:2).

An oligonucleotide target that was complementary to these oligonucleotides was synthesized and labeled at the 5'-end with $^{32}P$ The $^{32}P$-labeled oligonucleotide (0.2 pmol) was added to three tubes that contained 25 pmol of either NAX3220, NAX3272, or NAX3273. The final volume in each tube was then made up to 0.2 mL by the addition of formamide and NaCl solutions to give final Na+ and formamide concentrations of 0.75 M and 21.5% (v/v), respectively.

The contents of each tube were transferred to individual wells of a 96-well microtiter plate and heated to 40° C. The samples were then irradiated for up to 1200 s using 350 nm UV lamps in a UV light box (UVP). The lamps were situated ~2.5 cm from the samples. Aliquots (10 µL) of the reaction mixtures were removed at 60, 150, 300, and 1200 s.

Upon completion of the reactions, the products were electrophoresed through 15% polyacrylamide gels containing 7 M urea, and the gel was exposed to X-ray film overnight. Analysis of the film indicated that the $^{32}P$-labeled target in each lane migrated through the gel to form two distinct bands. The relative proportions of the two bands depended on the irradiation time. The amount of the faster moving band (unreacted target) decreased upon increased irradiation time whereas the slower moving band (crosslinked target) increased.

The amount of crosslinked product formed at each time point was quantified by cutting out the radioactive bands from the gel and counting them in a scintillation counter. The following results were obtained for the three reactions:

| | Crosslinking (%) | | |
|---|---|---|---|
| UV Irradiation (s) | NAX3220 (XL51) | NAX3272 (XL52) | NAX3273 (XL53) |
| 60 | 15.2 | 13.5 | 16.6 |
| 150 | 32.1 | 29.6 | 37.5 |
| 300 | 50.2 | 47.0 | 58.7 |
| 1200 | 83.0 | 82.8 | 88.4 |

The data showed that the oligonucleotide containing XL53 (NAX3273) reacted faster than the oligonucleotide containing XL51 (NAX3220), which in turn reacted faster than the oligonucleotide containing XL52 (NAX3272). After 150 s irradiation, NAX3273 had reacted with the target to yield ~1.17-fold as much crosslinked product as NAX3220 and ~1.27-fold as much crosslinked product as NAX3272.

Preparation of XL53

(2R)Glycidyl 6-(4-methylcoumarinyl)ether

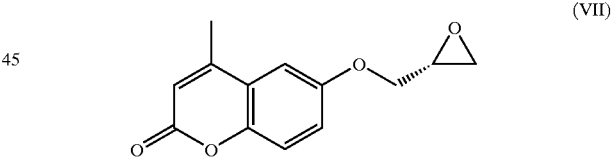

(VII)

1.56 g (8.9 mmol) 6-hydroxy-4-methylcoumarin and 1.6 g potassium carbonate were combined in a solvent mixture composed of 30 mL dry dimethyl-formamide and 30 mL acetone. The resulting solution was heated to reflux, after which 2.5 g (9.6 mmol) (2R)-(−)-glycidyl 3-nitrobenzenesulfonate was added to the solution. The reaction mixture was heated at 50–60° C. for 3 hr with stirring. To the solution was added 30 mL ethyl acetate and 30 mL water, resulting in precipitate formation. The solid was filtered, and the organic phase was saved. The aqueous phase was extracted with 4×25 mL ethyl acetate. The combined organic phase was dried over sodium sulfate. After filtration, solvent evaporation yielded crude product as a solid. This material was recrystallized from ethyl acetate:ethanol:acetone (30:5:5) to yield 0.76 g (37% yield) product. Additional product was obtained from the mother liquor.

(2R)-1-O-(6-(4-Methylcoumarinyl))glycerol (XL53)

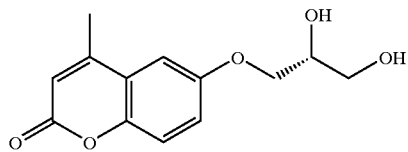

(VIII)

420 mg (1.8 mmol) compound VII was added to a solution containing 32 mL acetone and 12 mL 2 M sulfuric acid. The resulting solution was heated at 50–60° C. for 20 min with stirring. The acetone was removed from the reaction mixture by rotary evaporation. The remaining aqueous solution was neutralized to pH 7 by the addition of 10% sodium hydroxide. The neutralized solution was extracted with ethyl acetate. Evaporation of the ethyl acetate yielded 350 mg of crude product (78% yield).

(2R)-1-O-(6-(4-Methylcoumarinyl))-3-O-(4,4'-dimethoxytrityl)glycerol

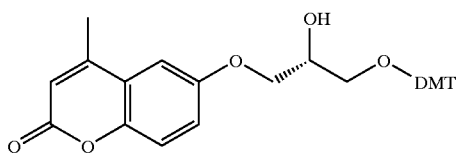

(IX)

350 mg (1.4 mmol) compound VI was dried by the addition of 1 mL pyridine followed by evaporation under vacuum. To the resulting solid was added 0.24 mL triethylamine, 11 mL pyridine, 480 mg (1.4mmol) 4,4'-dimethoxytrityl chloride (DMTCl), and a catalytic amount of N,N-dimethylaminopyridine The resulting solution was stirred at room temperature for 3 hr. To this solution was added 25 mL ethyl acetate containing 1% triethylamine. The solution was extracted with 3×15 mL saturated sodium chloride. The combined organic phase was dried over sodium sulfate. After filtration and solvent evaporation, approximately 1 g crude product was obtained. This material was purified by silica gel chromatography using ethyl acetate:hexane:triethylamine (20:80:1) to yield 200 mg (26% yield) product.

(2R)-1-O-(6-(4-Methylcoumarinyl))-2-O-(2-yanoethyl diisopropylphosphoramidite)-3-O-(4,4'-dimethoxytrityl) glycerol

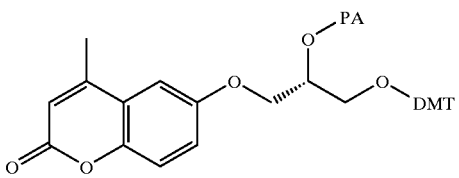

(X)

200 mg (0.36 mmol) compound IX was dried by the addition of pyridine followed by evaporation under vacuum. To the resulting solid was added under a dry argon atmosphere a solution containing 0.3 mL diisopropylethylamine in 3 mL methylene chloride. To this solution was added dropwise 0.3 mL (1.3 mmol) 2-cyanoethyl diisopropylchlorophosphoramidite (PACl). After 20 min, the reaction was diluted with 10 mL ethyl acetate containing 1% triethylamine. The solution was extracted with 3×10 mL water. The combined organic phase was dried over sodium sulfate. After filtration and solvent evaporation, crude product was obtained. This material was purified by silica gel chromatography using ethyl acetate:hexane:triethylarnine (15:80:1 to 25:75:1) to yield 250 mg (92% yield) product.

Preparation of XL52

XL52, the enantiomer of XL53, was prepared by using (2S)-(+)-glycidyl 3-nitrobenzenesulfonate in the first step of the synthetic procedure described in this example.

The invention now being fully described, it will be apparent to one of ordinary skill in the art that many changes and modifications can be made thereto without departing from the spirit or scope of the appended claims.

All publications and patent applications mentioned in this specification, including the background, are herein incorporated by reference to the same extent as if each individual publication or patent application was specifically and individually indicated to be incorporated by reference.

Additionally, the teachings of U.S. Pat. No. 6,005,093 are incorporated herein in their entirety.

---

We claim:
1. A compound having the formula:

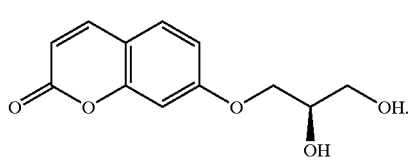

2. A compound having the formula:

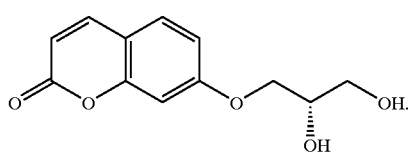

3. A compound having the formula:

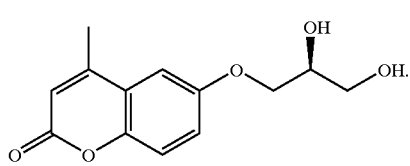

4. A compound having the formula:

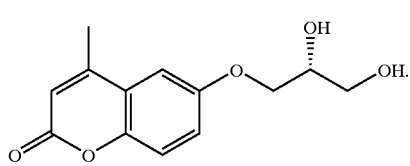

5. A compound having the formula:

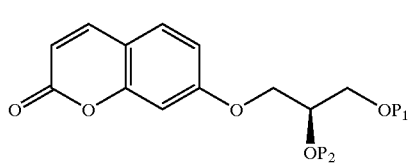

wherein $P_1$ and $P_2$, independently, are protecting groups.

6. The compound of claim 5, wherein $P_1$ is a trityl.
7. The compound of claim 5, wherein $P_2$ is a phosphoramidite.
8. The compound of claim 5, wherein $P_1$ is a trityl and $P_2$ is a phosphoramidite.

9. A compound having the formula:

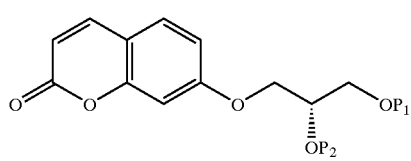

wherein $P_1$ and $P_2$, independently, are protecting groups.

10. The compound of claim 9, wherein $P_1$ is a trityl.
11. The compound of claim 9, wherein $P_2$ is a phosphoramidite.
12. The compound of claim 9, wherein $P_1$ is a trityl and $P_2$ is a phosphoramidite.

13. A compound having the formula:

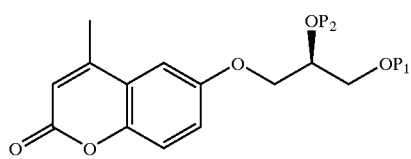

wherein $P_1$ and $P_2$, independently, are protecting groups.

14. The compound of claim 13, wherein $P_1$ is a trityl.
15. The compound of claim 13, wherein $P_2$ is a phosphoramidite.
16. The compound of claim 13, wherein $P_1$ is a trityl and $P_2$ is a phosphoramidite.

17. A compound having the formula:

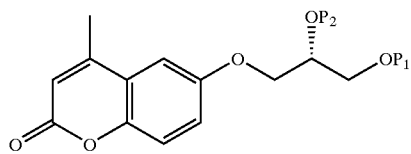

wherein $P_1$ and $P_2$, independently, are protecting groups.

18. The compound of claim 17, wherein $P_1$ is a trityl.
19. The compound of claim 17, wherein $P_2$ is a phosphoramidite.
20. The compound of claim 17, wherein $P_1$ is a trityl and $P_2$ is a phosphoramidite.

21. A compound having the formula:

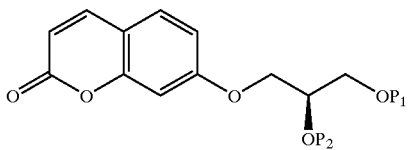

wherein one of $P_1$ and $P_2$ is a protecting group and the other is a hydrogen atom.

22. The compound of claim 21, wherein $P_1$ is a trityl.

23. The compound of claim 21, wherein $P_2$ is a phosphoramidite.

24. A compound having the formula:

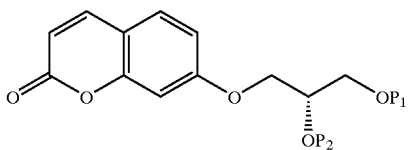

wherein one of $P_1$ and $P_2$ is a protecting group and the other is a hydrogen atom.

25. The compound of claim 24, wherein $P_1$ is a trityl.

26. The compound of claim 24, wherein $P_2$ is a phosphoramidite.

27. A compound having the formula:

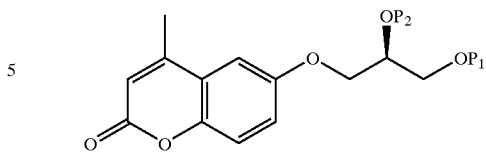

wherein one of $P_1$ and $P_2$, is a protecting group and the other is a hydrogen atom.

28. The compound of claim 27, wherein $P_1$ is a trityl.

29. The compound of claim 27, wherein $P_2$ is a phosphoramidite.

30. A compound having the formula:

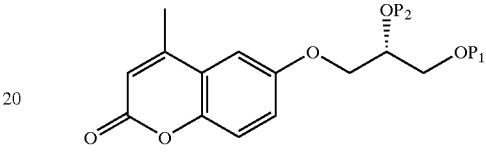

wherein one of $P_1$ and $P_2$, is a protecting group and the other is a hydrogen atom.

31. The compound of claim 30, wherein $P_1$ is a trityl.

32. The compound of claim 30, wherein $P_2$ is a phosphoramidite.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: "n" represents a non-nucleoside coumarin
       derivative.

<400> SEQUENCE: 1
aaaanacata caccttacag ctt                                           23

<210> SEQ ID NO 2
<211> LENGTH: 23

```
-continued

<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (22)..(22)
<223> OTHER INFORMATION: "n" represents a non-nucleoside coumarin
      derivative.

<400> SEQUENCE: 2
taaaacagaa acgcgtaccg ana                                          23
```